(12) United States Patent
Lagos González (10) Patent No.: US 8,952,152 B2
(45) Date of Patent: Feb. 10, 2015

(54) METHODS FOR PURIFYING PHYCOTOXINS, PHARMACEUTICAL COMPOSITIONS CONTAINING PURIFIED PHYCOTOXINS, AND METHODS OF USE THEREOF

(75) Inventor: Marcelo Santiago Lagos González, Santiago (CL)

(73) Assignee: Proteus S.A., Santiago (CL)

(*) Notice: Subject to any disclaimer, the term of this patent is extended or adjusted under 35 U.S.C. 154(b) by 114 days.

(21) Appl. No.: 13/243,153

(22) Filed: Sep. 23, 2011

(65) Prior Publication Data

US 2012/0065217 A1 Mar. 15, 2012

Related U.S. Application Data

(63) Continuation-in-part of application No. PCT/IB2010/051187, filed on Mar. 18, 2010, and a continuation-in-part of application No. PCT/IB2010/051188, filed on Mar. 18, 2010.

(51) Int. Cl.

| | |
|---|---|
| *C07D 487/14* | (2006.01) |
| *C12N 1/12* | (2006.01) |
| *C12P 17/18* | (2006.01) |

(52) U.S. Cl.

CPC ................ *C12N 1/12* (2013.01); *C07D 487/14* (2013.01); *C12P 17/182* (2013.01)

USPC ........................................................ 544/251

(58) Field of Classification Search

CPC ...................................................... C07D 487/14

USPC .......................................... 514/267; 544/251

See application file for complete search history.

(56) References Cited

U.S. PATENT DOCUMENTS

| | | | |
|---|---|---|---|
| 3,004,894 | A | 10/1961 | Johnson |
| 3,328,259 | A | 6/1967 | Anderson |
| 3,374,144 | A | 3/1968 | Emmanuel |
| 3,957,996 | A | 5/1976 | Adams |
| 3,966,934 | A | 6/1976 | Adams |
| 4,001,413 | A | 1/1977 | Adams |
| 4,022,899 | A | 5/1977 | Adams |
| 4,029,793 | A | 6/1977 | Adams |
| 4,029,794 | A | 6/1977 | Adams |
| 4,313,958 | A | 2/1982 | LaHann |
| 4,401,663 | A | 8/1983 | Buckwalter |
| 4,443,473 | A | 4/1984 | Buckwalter |
| 4,460,602 | A | 7/1984 | Buckwalter |
| 4,493,848 | A | 1/1985 | LaHann |
| 4,537,776 | A | 8/1985 | Cooper |
| 4,544,668 | A | 10/1985 | Janusz |
| 4,544,669 | A | 10/1985 | LaHann |
| 4,564,633 | A | 1/1986 | LaHann |
| 4,654,323 | A | 3/1987 | Beitner |
| 4,820,720 | A | 4/1989 | Sanders |
| 4,863,970 | A | 9/1989 | Patel |
| 4,973,468 | A | 11/1990 | Chiang |
| 4,997,853 | A | 3/1991 | Bernstein |
| 5,006,342 | A | 4/1991 | Cleary |
| 5,008,289 | A | 4/1991 | Bernstein |
| 5,013,759 | A | 5/1991 | Berman |
| 5,045,565 | A | 9/1991 | Gardner |
| 5,099,030 | A | 3/1992 | Gardner |
| 5,134,166 | A | 7/1992 | Bernstein |
| 5,618,563 | A | 4/1997 | Berde |
| 5,700,485 | A | 12/1997 | Berde |
| 5,716,637 | A | 2/1998 | Anselem |
| 5,858,397 | A | 1/1999 | Lim |
| 6,030,974 | A | 2/2000 | Schwartz |
| 6,326,020 | B1 | 12/2001 | Kohane |
| 6,407,088 | B1 | 6/2002 | Dong |
| 6,455,066 | B1 | 9/2002 | Fischer |
| 6,673,363 | B2 | 1/2004 | Luo |
| 2002/0161013 | A1 | 10/2002 | Liu |
| 2002/0197284 | A1 | 12/2002 | Luo |
| 2004/0172354 | A1 | 9/2004 | Charnley |
| 2005/0202093 | A1 | 9/2005 | Kohane |

(Continued)

FOREIGN PATENT DOCUMENTS

| | | |
|---|---|---|
| BE | 776769 | 12/1971 |
| EP | 0043738 | 9/1982 |

(Continued)

OTHER PUBLICATIONS

Pomati, F., et al. "Evidence for differences in the metabolism of saxitoxin and C1+2 toxins in the freshwater cyanobacterium *Cylindrospermopsis raciborskii* T3." Biochmica et Biophysica. 1674 (2004), pp. 60-67.*

(Continued)

*Primary Examiner* — Andrew D Kosar
*Assistant Examiner* — John S Kenyon
(74) *Attorney, Agent, or Firm* — Pabst Patent Group LLP

(57) ABSTRACT

Phycotoxins are purified from a mixture of phycotoxins produced in a continuous process. Cyanobacteria are produced in a continuous culture, then lyzed, the cells pelleted and extracted, and the extract purified using an organic solvent-aqueous mixture and repeated passage through a diatomaceous earth column. The column is washed with acetic acid, then the neosaxitoxin extracted with an alcohol-water mixture. The eluate is passed through activated charcoal columns, which are washed with distilled water to remove the retained pigments and impurities, the further purified by HPLC. In one embodiment, the process produces only neosaxitoxin and saxitoxin. In another embodiment, the process produces only GTX2/3.

8 Claims, 6 Drawing Sheets

(56) References Cited**

U.S. PATENT DOCUMENTS

| | | | |
|---|---|---|---|
| 2005/0214325 A1* | 9/2005 | David | 424/239.1 |
| 2006/0271466 A1 | 11/2006 | Gorbatovsky | |
| 2008/0045553 A1 | 2/2008 | Wilson | |
| 2008/0154792 A1 | 6/2008 | Maggioncalda | |

FOREIGN PATENT DOCUMENTS

| | | |
|---|---|---|
| EP | 750909 | 1/1997 |
| GB | 1370904 | 10/1974 |
| GB | 2153223 | 8/1985 |
| WO | 8505621 | 12/1985 |
| WO | 9311798 | 6/1993 |
| WO | 9401166 | 1/1994 |
| WO | 9405265 | 3/1994 |
| WO | 9641616 | 12/1996 |
| WO | 9851290 | 11/1998 |
| WO | 0141550 | 6/2001 |
| WO | WO 0222129 A1 * | 3/2002 |
| WO | 0241915 | 5/2002 |
| WO | 2006034624 | 4/2006 |
| WO | 2006091719 | 8/2006 |
| WO | 2008063603 | 5/2008 |
| WO | 2009143174 | 11/2009 |
| WO | 2009143175 | 11/2009 |
| WO | 2010041255 | 4/2010 |
| WO | 2010109386 | 9/2010 |
| WO | 2010109387 | 9/2010 |
| WO | 2010117996 | 10/2010 |
| WO | 2010129864 | 11/2010 |

OTHER PUBLICATIONS

Llewellyn, L.E., et al. "Saxitoxin, a toxic marine natural product that targets a multitude of receptors." Natural Product Reports. vol. 23, (2006), pp. 200-222.*

Stewart, J.E., et al. "Phycotoxins: Physiology and Production." © 2004. Available from: <http://web.archive.org/web/20040118221536/http://www.mar.dfo-mpo.gc.ca/science/review/e/pdf/phycotoxins.pdf>.*

("Solid Phase Extraction Columns—Reversed Phase." (c) Nov. 2006. Available from: <http://web.archive.org/web/20061108080659/http://www.chromtech.com/Catalog7/ProductLine/PDF_Files/256_263.pdf>.*

Livingston, R.S., et al. "Isolation and Characterization of Host-Selective toxin from *Helminthosporium sacchari*." J. Biol. Chem. (Feb. 25, 1981), vol. 256, No. 4, pp. 1705-1710.*

Bolch and Blackburn, "Isolation and purification of Australian isolates of the toxic cyanobacterium*Microcystis aeruginosa* Kütz", J. Appl. Phycology, 8, 5-13 (1996).

Castro, at al., "The effect of temperature on growth and production of paralytic shellfish poisoning toxins by the cyanobacterium *Cylindrospermopsis raciborskii* C10", Toxicon, 44:483-89 (2004).

Guevremont, et al., "Comparison of cation-exchange and chelating cation-exchange resins for the concentration of saxitoxin", Analy. Chimica Acta., 255:163-68 (1991).

Llewellyn, "Saxitoxin, a toxic marine natural product that targets a multitude of receptors", Nat, Prod. Rep., 23:200-222 (2006).

Long, et al., "Cellular microcystin content in N-Limited *Microcystis aerginosa* can be predicted from growth rate", Appl. Enviro. Microbiol., 67(1):278-83 (2001).

Media recipes used in CMAR,CMAR Methods. Retrieved Aug. 2, 2008 http:// www.marine.csiro.au/microalgae/methods/Media%20CMARC%20recipes.htm, (c) 2008.

Pomati, et al., "The purine degradation pathway: possible role in paralytic shellfish toxin metabolism in the cyanobacterium *Planktothrix* sp. FP1", Environ. Int., 27:463-470 (2001).

Pomati, et al., "Evidence for differences in the metabolism of saxitoxin and C1+2 toxins in the freshwater cyanobacterium *Cylindrospermopsis raciborskii* T3", Biochem.Biophys.Acta., 1674:60-67 (2004).

Rositano, et al., Ozonation of nom and algal toxins in four treated waters, Wat. Rev., 35(1):23-32 (2001).

Soto, et al., "The effects of chloramphenicol, arginine and temperature on PST-production by *Cylindrospermopsis raciborskii* strain D9", Proceedings of the 12th Intl. Conf. on Harmful Algae, Copenhagen (2008).

Sayfritz, et al., "Determination of paralytic shellfish poisoning toxins in Norwegian shellfish by liquid chromatography with fluorescence and tandem mass spectrometry detection", Toxicom, 52:330-40 (2008).

International Search Reoport PVT/IB2010/051188, (c) 2010.

Aboul-Fadl, "Antisense oligonucleotides: the state of the art", Curr Med Chem 12:2193-214 (2005).

Akerman, et al., "Penetration enhancers and othe factors governing percutaneous local anaesthesia with lidocaine", Acta Pharma. Et toxicological, 45(1):58-65 (1979).

Adjei and Garren, "Pulmonary delivery of peptide drugs: effect of particle size on bioavailability of leuprolide acetate in healthy male volunteers", J Pharm. Res, 7:565-9 (1990).

Alam, et al., "Design of liposome to improve encapsulation efficiency of gelonin and its effect on immunoreactivity and ribosome inactivating property", Mol Cell Biochem 112:97-107 (1992).

Barnes, "Sativex: clinical efficacy and tolerability in the treatment of symptoms of multiple sclerosis and neuropathic pain", Expert Opin Pharmacother 7:607-15 (2006).

Barnet, et al., "Tissue injury from tricyclic antidepressants used as local anesthetics" Anesth Analg, 101(6):1838-1843 (2005).

Barnet, et al., "Site 1 sodium channel blockers prolong the duration of sciatic nerve blockade from tricyclic antidepressants", Pain 110:432-8 (2004).

Bartlett, "Phosphorus assay in column chromatography", J. Biol. Chem., 234 (3):466-468 (1959).

Bates, et al., "A chemical assay for saxitoxin. Improvements and modifications", J. of agricultural and food chem., 26(1):252-254 (1978).

Befort, et al., "Selective up-regulation of the growth arrest DNA damage-inducible gene Gadd45 alpha in sensory and motor neurons after peripheral nerve injury", Eur J Neurosci., 18(4):911-922 (2003).

Benoit, et al., "Pharmacologic correlation between local anesthetic-induced myotoxicity and disturbances of intracellular calcium distribution", Toxicol. Appl. Pharmacol., 52:187-198 (1980).

Berde, et al., "Tetrodotoxin-bupivacaine-epinephrine combinations for prolonged local anesthesia", Marine Drugs, 9:2717-28 (2011).

Bernards and Hill, "Physical and chemical properties of drug molecules governing their diffusion through the spinal meninges", Anesthesiology, 77 (4):750-6 (1992).

Binshtok, et al., "Inhibition of nociceptors by TRPV1-mediated entry of impermeant sodium channel blockers", Nature, 449:607-610 (2007).

Cereda, et al., "Liposomal formulations of prilocaine, lidocaine and mepivacaine prolong analgesic duration", Can J Anaesth., 53(11):1092-1097 (2006).

Chaim-Matyas, et al., "Encapsulation of the cobra cytotoxin P4 in liposomes", Biotechnol Appl Biochem, 17( Pt 1):31-6 (1993).

Choi and Maibach, "Liposomes and niosomes as topical drug delivery systems", J. Pharmacal and Biophys. Res.,18(5):209-19 (2005).

Clarkson, et al., "Mechanism for bupivacaine depression of cardiac conduction: fast block of sodium channels during the action potential with slow recovery from block during diastole", Anesthesiology, 62:396-405 (1985).

Cortesi, et al., "Sugar cross-linked gelatih for controlled release: microspheres and disks", Biomaterials 19:1641-9 (1998).

de Araujo, et al., "Encapsulation of mepivacaine prolongs the analgesia provided by sciatic nerve blockade in mice", Can J Anaesth., 51(6):566-572 (2004).

de Paiva and Dolly, "Light chain of botulinum neurotoxin is active in mammalian motor nerve terminals when delivered via liposomes", FEBS Lett 277:171-4 (1990).

Drager, et al., Prolonged intercostal nerve blockade in sheep using controlled-release of bupivacaine and dexamethasone from polymer microspheres Anesthesiology, 89(4):969-979 (1998).

(56) References Cited

OTHER PUBLICATIONS

Epstein-Barash, et al., "Prolonged duration local anesthesia with minimal toxicity", PNAS, 106(17):7125-30 (2009).
Estebe, et al., "Amitriptyline neurotoxicity: dose-related pathology after topical application to rat sciatic nerve", Anesthesiology, 100:1519-25 (2004).
Fang, et al., "Synergistically enhanced transdermal prrmration and tropical analgesia of tetracaine gel containing menthol and ethanol in experimental and clinical studies", Eu J Pharm and Biopharm., 68:735-40 (2008).
Fisher, et al.,"Detection of intravascular injection of regional anaesthetics in children", Can. J. Anaesth., 44: 592-8 (1997).
Flores, Production of ammonium dependent on basic L-amino acids vy anacystis nidulans, Arch Microbiol, 131:91-4 (1982).
Fozzard, et al., "Mechanism of local anesthetic drug action on voltage-gated sodium channels", Curr. Pharm. Des., 11:2671-2686 (2005).
Fraser, et al., "Intravesical liposome administration—a novel treatment for hyperactive bladder in the rat", Urology, 61: 656-663 (2003).
Freitas and Frezard, "Encapsulation of native crotoxin in liposomes: a safe approach for the production of antivenom and vaccination against *Crotalus durissus terrificus* venom", Toxicon 35:91-100 (1997).
Garcia, et al., "Route of metabolization and detoxicarion of paralytric shellfish toxins in humans", Toxicon, 55:135-44 (2010).
Gerner, et al., "Amitriptyline versus bupivacaine in rat sciatic nerve blockade", Anesthesiology, 94(4):661-667 (2001).
Grant, et al., "A novel liposomal bupivacaine formulation to produce ultralong-acting analgesia", Anesthesiology, 101(1):133-137 (2004).
Grant, et al., "Analgesic duration and kinetics of liposomal bupivacaine after subcutaneous injection in mice", Clin Exp Pharmacol Physiol., 30(12):966-968 (2003).
Grant, et al., "DRV liposomal bupivacaine: preparation, characterization, and in vivo evaluation in mice", Pharm Res., 18(3):336-343 (2001).
Gregoradis, et al., "Engineering liposomes for drug delivery: progress and problems", Trends Biotechnol 13, 527-37 (1995).
Gregoriadis and Allison, "Entrapment of proteins in liposomes prevents allergic reactions in pre-immunised mice", FEBS Lett 45:71-4 (1974).
Gregoriadis and Ryman, "Liposomes as carriers of enzymes or drugs: a new approach to the treatment of storage diseases", Biochrem. J., 124:58P (1971).
Gregoriadis, et al., "Improving the therapeutic efficacy of peptides and proteins: a role for polysialic acids", Intl. J. Pharm., 300:125-30 (2005).
Gregoriadis, "The carrier potential of liposomes in biology and medicine (second of two parts)", N Engl J Med 295:765-70 (1976).
Haller, et al., "Differential neurotoxicity of tricyclic antidepressants and novel derivatives in vitro in a dorsal root ganglion cell culture model", Eur J Anaesthesiol., 24(8):702-708 (2007).
Harden, "Chronic neuropathic pain. Mechanisms, diagnosis and treatment", The Neurologist, 11(2):111-22 (2005).
Hoebeeck, et al., "Rapid detection of VHL exon deletions using real-time quantitative PCR", Lab. Invest., 85(1):24-33(2005).
Hu, "Interactions of Neosaxitoxin with the sodium channel of the frog sketietal muscle fber", J Gen Physiology, 97:561-78 (1991).
Jia, et al., "Prolongation of sciatic nerve blockade by in situ cross-linked hyaluronic acid", Biomaterials, 25(19):4797-4804 (2004).
Kao, "Tetrodotoxin, saxitoxin and their significance in the study of excitation phenomena," Pharmacological Rev., 18(2):999-1049 (1966).
Kohane, et al., "A re-examination of tetrodotoxin for prolonged duration local anesthesia", Anesthesiology, 89:119-31 (1998a).
Kohane, et al., "Biocompatibility of lipid-protein-sugar particles containing bupivacaine in the epineurium", J Biomed Mater Res., 59(3):450-459 (2002).

Kohane, et al., "Effects of adrenergic agonists and antagonists on tetrodotoxin-induced nerve block", Reg Anesth Pain Med, 26:239-45 (2001).
Kohane, et al., "Prolonged duration local anesthesia from tetrodotoxin-enhanced local anesthetic microspheres", Pain,104(1-2):415-21 (2003).
Kohane, et al., "Sciatic nerve blockade in infant, adolescent, and adult rats: a comparison of ropivacaine with bupivacaine", Anesthesiology, 89:1199-1208 (1998b).
Kohane, et al., "The local anesthetic properties and toxicity of saxitonin homologues for rat sciatic nerve block in vivo", Reg Anesth Pain Med., 25:52-9 (2000).
Kohane, et al., "Vanilloid receptor agonists potentiate the in vivo local anesthetic activity of percutaneously injected site 1 sodium channel blockers", Anesthesiology, 90:524-34(1999).
Kushla, et al., "Noninvasive assessment of anesthetic activity of topical lidocaine formulations", J Pharm Sci, 82:1118-22 (1993).
Kuznicki, et al., "Structure of neosaxitoxin", Am Chem Soc., 0002-7863/7:6791-3 (1978).
Lagos, "The first evidence of paralytic shellfish toxins in the freshwater cyanobacteria *Cylindrospermopsis racivorski*", Toxicon, 37:1359-73 (1999).
Lim, et al. "The Quaternary Lidocaine Derivtive, QX-314, Produces Long-lasting Local Anesthesia in Animal Models In Vivo", Anesthesiology, 107:305-11 (2007).
Lirk, et al., "The neurotoxic effects of amitriptyline are mediated by apoptosis and are effectively blocked by inhibition of caspase activity", Anesth Analg., 102(6):1728-33 (2006).
Luo, et al., "Injury type-specific calcium channel alpha 2 delta-1 subunit up-regulation in rat neuropathic pain models correlates with antlallodynic effects of gabapentin", J Pharmacol Exp Ther., 303(3):1199-1205 (2002).
Malinovsky, et al., "A dose-response study of epidural liposomal bupivacaine in rabbits", J Control Release., 60(1):111-119 (1999).
Mandel and Lee, "Listeriolysin O-liposome-mediated cytosolic delivery of macromolecule antigen in vivo: enhancement of antigen-specific cytotoxic T lymphocyte frequency, activity, and tumor protection", Biochim Biophys Acta 1553:7-17 (2002).
Masters, et al., "Prolonged regional nerve blockade by controlled release of local anesthetic from a biodegradable polymer matrix" Anesthesiology, 79 (2):340-346 (1993).
Mazur-Marzec, "Characterization of phycotoxins produced by cyanobacteria", Intl J Oceanography and Hydrobiology, XXXV (1):85-109 (2006).
McLure and Rubin , "Review of local anaesthetic agents", Minerva Anesthesiol., 71:59-74 (2005).
Mearow, et al., "Stress-mediated signaling in PC12 cells—the role of the small heat shock protein, Hsp27, and Akt in protecting cells from heat stress and nerve growth factor withdrawal", Journal of neurochemistry, 83(2):452-462 (2002).
Middleton, "Mechanism of action of surfactants on water binding properties of isolated stratum corneum", J Soc Cosmet Chem. ,20:399-403 (1969).
Minko, et al., "New generation of liposomal drugs for cancer", Anticancer Agents Med Chem 6, 537-52 (2006).
Myers, et al., "Neurotoxicity of local anesthetics: altered perineurial permeability, edema, and nerve fiber injury", Anesthesiology, 64:29-35 (1986).
Nakagomi, et al., "Expression of the activating transcription factor 3 prevents c-Jun N-terminal kinase-induced neuronal death by promoting heat shock protein 27 expression and Akt activation", J Neurosci., 23(12):5187-5196 (2003).
Newton, et al., "Dorsal root ganglion neurons show increased expression of the calcium channel alpha2delta-1 subunit following partial sciatic nerve injury", Brain Res Mol Brain Res., 95(1-2):1-8 (2001).
Nixdrof, "Phytoplankton assemblages and steady state in deep and shallow eutropic lakes—an approach to differentiate the habitat properties of Oscillatoriales", Hydrobiologia, 502:111-21 (2003).
Olivera, et al., "Diversity of *Conus* Neuropeptides," Science, 249:257-63, (1990).
Oshima, "Postcolumn derivatization liquid chromatographic method for paralytic shellfish toxins", J of AOAC Intl., 78(2):528-32 (1995).

(56) References Cited

OTHER PUBLICATIONS

Padera, et al., "Tetrodotoxin for prolonged local anesthesia with minimal myotoxicity", Muscle Nerve, 34:747-53 (2006).
Padera, et al., "Local myotoxicity from sustained release of bupivacaine from microparticles", Anesthesiology, 108(5):921-928 (2008).
Pere, et al., "Local myotoxicity of bupivacaine in rabbits after continuous supraclavicular brachial plexus block", Reg Anesth, 18(5):304-307 (1993).
Ribaud, et al., "Organization of stratum corneum lipids in relation to permeability: influence of sodium lauryl sulfate and preheating", Pharm Res 11:1414-8 (1994).
Rodriguez-Navarro, et al., "Neosaxition as a local anesthetic", Anesthesiology, 106:339-45 (2007).
Rodriguez-Navarro, et al., "Potenriation of local anethetic activity of neosaxitoxin with bupivacaine or epinephrine developmenr of a long-acting pain blacker", Neurotox. Res., 16:408-15 (2009).
Rodriguez-Navarro, et al., "Comparison of neosaxitoxin versus bupivacaine via port infiltration for postoperarive analgesia following laparoscopic cholecystectomy", Reg. Anesth. Pain Med., 36:103-9 (2011).
Ruetsch., et al., "From cocaine to ropivacaine: the history of local anesthetic drugs", Curr. Top. Med. Chem., 1:175-182 (2001).
Sagie and Kohane, "Prolonged sensory-selective neve blockade", Natl. Acad. Sci, 107(8):3740-5 (2010).
Sakura, et al., "Local anesthetic neurotoxicity does not result from blockade of voltage-gated sodium channels", Anesth Anaig., 81;338-46 (1995).
Sapra, et al., "Ligand-targeted liposomes for cancer treatment", Curr. Drug Deliv., 2:369-81 (2005).
Schneider, et al., "A preferential inhibition of impulses in C-fibers of the rabbit vagus nerve by veratridine, an activator of sodium channels," Anesthesiology,74:270-81 (1991).
Scholz, "Mechanisms of (local) anaesthetics on voltage-gated sodium and other ion channels", Br J. Anaesth., 89:52-61 (2002).
Scurlock, et al. "Tetraethylammonium derivatives: Ulatralong-acting Local Anesthetics", Anesthesiology, 54:265-9 (1981).
Shankarappa, et al., "Lipsome-encapsulated saxitoxin in the trearment of nerve injury-induced chronic neuropathic pain", 41st annual meeting Society-for-neuroscience, Nov. 12-16, Washington DC (2011).
Shankarappa, et al., "Prolonged nerve blockage delays the onset of neuropathic pain", PNAS, 109(43):17555-60 (2012b).
Shankarappa, et al., "Duration and local toxicity of sciatic nerve blockade with coinfected site 1 sodium-channel blockers and quaternary lidocaine derivatives", Reg. Anesthesia Pain Med., 37(5):483-9 (2012a).
Shimizu, "Biosynthesis of red tide toxins", Marine Toxins, 418:21-8 (1990).
Simons, et al., "Effect of chemical permeation enhancers on nerve blockade", Mol Pharmaceutics, 6:265-73 (2009).
Sleno, et al., "Gas-phase dissociation reactions of protonated saxitoxin and neosaxition", J am Soc Mass Spectrom, 15:462-77 (2004).
Soares, et al., "Neuronal and glial expression of the adhesion molecule TAG-1 is regulated after peripheral nerve lesion or central neurodegeneration of adult nervous system", Eur J Neurosci., 21(5):1169-1180 (2005).
Song, at al., "Axotomy-induced dopaminergic neurodegeneration is accompanied with c-Jun phosphorylation and activation transcription factor 3 expression", Exp Neurol., 209(1):268-278 (2008).
Strichartz, "Structural determinanrs of affinity of saxitoxin for neuronal sodium channels", J Gen. Physiol., 84:281-305 (1984).
Szoka, et al., "Comparative properties and methods of preparation of lipid vesicles (liposomes)", Annual review of biophysics and bioengineering, 9:467-508 (1980).
Thalhammer, et al., "Neurologic evaluation of the rat during sciatic nerve block with lidocaine," Anesthesiology, 82(4):1013-25 (1995).
Tyagi, et al., "Urodynamic and immunohistochemical evaluation of intravesical capsaicin delivery using thermosensitive hydrogel and liposomes", J Urol 171:483-9 (2004).
Vandesompele, et al., "Accurate normalization of real-time quantitative RT-PCR data by geometric averaging of multiple internal control genes", Genome biology, 3(7):RESEARCH0034 (2002).
Wagner, et al., "Salitoxin and Procaine Act Independently on Separate Sites of the Sodium Channel," Pflugers Arch., 364:65-70 (1976).
Wall, et al., "Autonomy following peripheral nerve lesions: experimental anesthesia dolorosa", Pain., 7(2)103-111 (1979).
Wylie, et al., "Respiratory and neuromuscular effects of neosaxition in anesthetized sheep", Abstract for presentation at the ASA annual meeting, 3 pages, Oct. 2011.
Wylie, et al., "Respirarory, neuromuscular, and cardiovascular effects of neosaxitoxin in isoflurane-anesthetized sheep", Reg. Anes. Pain Med., 00:1-7 (2012).
Wu, et al., Lipid-based nanoparticulate drug delivry sysrems. In D Thassu (Ed.), Nanoparticulate Drug Delivery Systems, pp. 89-98 (2007).
Yahalom, et al., "Spinal anesthesia in infant rats: development of a model and assessment of neurologic outcomes", Anesthesiology, 114(6):1325-35 (2011).
Yamashita, et al., "A comparison of the neurotoxic effects on the spinal cord of tetracaine, lidocaine, bupivacalne, and ropivacaine administered intrathecally in rabbits", Anesth Analg, 97(2):512-519 (2003).
Zanen, et al., "The optimal particle size for parasympathicolytic aerosols in mild asthmatics", Int J Pharm., 114:111-5. (1995).
Zimmer, et al., "Cardiotoxic and neurotoxic effects after accidental intravascular bupivacaine administration. Therapy with lidocaine propofol and lipid emulsion", Anaesthesist, 56(5):449-453 (2007).
Zimmermann, "Ethical guidelines for investigations of experimental pain in conscious animals", Pain, 16(2):109-110 (1983).

* cited by examiner

FIG. 5

STD NLG 9/13
10 μL

| | | |
|---|---|---|
| 1 | 8.847 | 765.0926 |
| 2 | 10.820 | 3323.3249 |
| 3 | 11.800 | 1208.5950 |
| 4 | 14.087 | 11392.8204 |
| 5 | 17.587 | 16678.3203 |

FIG. 6

| | | |
|---|---|---|
| 1 | 8.873 | 1016.8684 |
| 2 | 10.927 | 5262.1901 |
| 3 | 13.260 | 11837.7101 |
| 4 | 16.647 | 36388.1650 |

10 ul, Botella 3 500 ml
GTX 3/2 pH 3.0 (NaCl 0.9%),
DIL 1/3000

METHODS FOR PURIFYING PHYCOTOXINS, PHARMACEUTICAL COMPOSITIONS CONTAINING PURIFIED PHYCOTOXINS, AND METHODS OF USE THEREOF

CROSS REFERENCE TO RELATED APPLICATIONS

This application claims priority under 35 U.S.C. 371 to PCT/IB2010/051187 filed Mar. 18, 2010, PCT/IB2010/051188 filed Mar. 18, 2010, Chilean Patent Application No. 723-2009 filed Mar. 24, 2009, and Chilean Patent Application No. 722-2009 filed Mar. 24, 2009, all of which are incorporated by reference.

FIELD OF THE INVENTION

This invention is in the field of methods of purification of phycotoxins from natural sources, particularly methods for the continuous production and purification of phycotoxins from cyanobacteria and use of the purified phycotoxins in pharmaceutical compositions.

BACKGROUND OF THE INVENTION

Phycotoxins ([phyco=seaweeds and algae] plus toxins) are a diverse group of substances produced by various aquatic plants in marine and fresh waters throughout the world. Not all aquatic plants produce toxins; and among those that do, not all, even from the same genera and species, produce toxins at all times and under all circumstances. Such toxins are associated with large fish kills and major kills of marine mammals. These toxins can also be found in shellfish.

Neosaxitoxin and saxitoxin are two specific phycotoxins produced by dinoflagellate species of the genera *Alexandrium* sp., *Piridinium* sp. and *Gimnodinium* sp. and cyanobacteria.

Neosaxitoxin and saxitoxin acts as specific blockers of the voltage-dependent sodium channels present in excitable cells. Due to the inhibition of sodium channels, the transmission of a nervous impulse is blocked preventing the release of neurotransmitters at the neuromotor junction, which prevents muscular contraction. Due to these physiological effects, these compounds are potentially useful in pharmacology when used as muscular activity inhibitors in pathologies associated with muscular hyperactivity, such as muscular spasms and focal dystonias, when administered locally. These compounds can also inhibit sensory pathways and generate an anesthetic effect when administered locally.

However, these compounds are not available commercially in the quantities necessary to manufacture pharmaceutical compositions. Therefore, there exists a need for improved methods to produce and purify phycotoxins having a definite compositional profile, particularly phycotoxin mixtures containing only neosaxitoxin and saxitoxin or GTX 2 and GTX 3.

Therefore, it is an object of the invention to improved methods for producing and purifying phycotoxins having a definite compositional profile, particularly phycotoxin mixtures containing only neosaxitoxin and saxitoxin or GTX 2 and GTX 3.

It is also an object of the invention to provide pharmaceutical compositions containing the purified phycotoxin(s) and methods of use thereof

SUMMARY OF THE INVENTION

Phycotoxins are purified from a mixture of phycotoxins produced in a continuous process. Cyanobacteria are produced in a continuous culture, then lyzed, the cells pelleted and extracted, and the extract purified using an organic solvent-aqueous mixture and repeated passage through a diatomaceous earth column. The column is washed with acetic acid, and the phycotoxin(s) (e.g., neosaxitoxin) extracted with an alcohol-water mixture. The eluate is passed through activated charcoal columns, which are washed with distilled water to remove the retained pigments and impurities, and further purified by HPLC.

In a particular embodiment, the phycotoxins are produced in a continuous process in which one or more organic nutrients are added to the culture medium in order to form a mixture of phycotoxins having a definite compositional profile. In one embodiment, the process produces only neosaxitoxin and saxitoxin. In another embodiment, the process produces only GTX2/3.

Pharmaceutical compositions containing the purified phycotoxin(s) are also described herein. The compound(s) can be combined with one or more pharmaceutically acceptable excipients to prepare pharmaceutical compositions. The compounds can be formulated for parenteral administration, such as intravenous administration. In another embodiment, the compound(s) are formulated in an implant, such as an implant that provides extended or sustained release of the compound(s).

DETAILED DESCRIPTION OF THE INVENTION

I. Definitions

"Definite compositional profile", as used herein, refers to a mixture of particular phycotoxins. For example, a definite compositional profile can refer to a mixture containing only one, two, or three phycotoxins. In one embodiment, the mixture contains only two phycotoxins. In one embodiment, the mixture contains only neosaxitoxin (NEO) and saxitoxin (STX), wherein NEO is the major component (e.g., at least 60-80%). In another embodiment, the mixture contains only GTX2 and GTX3, wherein GTX 2 is the major component.

"Substantially pure", as used herein, means greater than 90, 91, 92, 93, 94, 95, 96, 97, 98, 99, 99.1, 99.2, 99.3, 99.4, or 99.5% purity. "Substantially pure" is typically used to describe the purity of one phycotoxin relative to one or more other phycotoxins, for example, the purity of neosaxitoxin relative to saxitoxin.

II. Methods of Purifying Phycotoxins

Methods of purifying phycotoxins, particularly phycotoxins produced in a continuous process, are described herein. The purified phycotoxins are suitable for use in pharmaceutical compositions and/or cosmetic applications.

A. Purification Steps

In one embodiment, phycotoxins are purified from a mixture of phycotoxins produced in a continuous process. In a particular embodiment, the phycotoxins are produced in a continuous process in which one or more organic nutrients are added to the culture medium to form a mixture of phycotoxins having a definite compositional profile. In one embodiment, the process produces only neosaxitoxin and saxitoxin. In another embodiment, the process produces only GTX2/3. The production process is described in PCT/IB2010/05186. The purification methods maintain the pharmacological activity of the phycotoxin(s) and provide a means for purifying phycotoxins on a commercial scale.

B. Production of Phycotoxin

Useful cyanobacteria are from genera *Cylindrospermopsis* sp, *Anabaena* sp, *Gomophosphaeria* sp, *Oscillatoria* sp, *Aphanizomenon* sp, *Lyngbya* sp, and combinations thereof. In a preferred embodiment, the species is *Cylindrospermopsis raciborskii, Anphanizomenon flos-aquae, Aphanizomenon* (APh) *issatschenkoi* (usaceb) Proskina-Lavrenco, *Aphanizomenon gracile* (*Lemm*) Lemm, *Anabaena circinalis, Lyngbya wollei*, and combinations thereof. In the most preferred embodiment, the cyanobacterium is *Aphanizomenon gracile* (*Lemm*) Lemm.

Phycotoxins can be produced in a continuous culture of *Aphanizomenon gracile*. The organisms are harvested from the culture using centrifugation or filtration to produce a cell pellet. The phycotoxin can be extracted from the cell pellet as well as the supernatant.

C. Extraction of Phycotoxin from Cells

1. Lysis of the Cells

The cell pellet is treated to lyze the cell walls. The cell wall can be lyzed using a solvent, such as one or more organic solvents. In a preferred embodiment, this is achieved using a mixture of organic solvents such as 1:1 chloroform:methanol+50 mM acetic acid in a 50% proportion with chloroform:methanol, pH 5.0, added to the cell pellet. Other methods including mechanical lysis can be used to break the cell wall.

Several methods are commonly used to physically lyse cells, including mechanical disruption, liquid homogenization, high frequency sound waves, freeze/thaw cycles and manual grinding.

Liquid-based homogenization is the most widely used cell disruption technique for small volumes and cultured cells. Cells are lysed by forcing the cell or tissue suspension through a narrow space, thereby shearing the cell membranes. Three different types of homogenizers are in common use. A Dounce homogenizer consists of a round glass pestle that is manually driven into a glass tube. A Potter-Elvehjem homogenizer consists of a manually or mechanically driven PTFE pestle shaped to fit a rounded or conical vessel. The number of strokes and the speed at which the strokes are administered influences the effectiveness of Dounce and Potter-Elvehjem homogenization methods. Both homogenizers can be obtained in a variety of sizes to accommodate a range of volumes. A French press consists of a piston that is used to apply high pressure to a sample volume of 40 to 250 ml, forcing it through a tiny hole in the press. Only two passes are required for efficient lysis due to the high pressures used with this process. The equipment is expensive, but the French press is often the method of choice for breaking bacterial cells mechanically.

Sonication is the third class of physical disruption commonly used to break open cells. The method uses pulsed, high frequency sound waves to agitate and lyse cells, bacteria, spores and finely diced tissue. The sound waves are delivered using an apparatus with a vibrating probe that is immersed in the liquid cell suspension. Mechanical energy from the probe initiates the formation of microscopic vapor bubbles that form momentarily and implode, causing shock waves to radiate through a sample. To prevent excessive heating, ultrasonic treatment is applied in multiple short bursts to a sample immersed in an ice bath. Sonication is best suited for volumes <100 ml.

The freeze/thaw method is commonly used to lyse bacterial and mammalian cells. The technique involves freezing a cell suspension in a dry ice/ethanol bath or freezer and then thawing the material at room temperature or 37° C. This method of lysis causes cells to swell and ultimately break as ice crystals form during the freezing process and then contract during thawing. Multiple cycles are necessary for efficient lysis, and the process can be quite lengthy. However, freeze/thaw has been shown to effectively release recombinant proteins located in the cytoplasm of bacteria and is recommended for the lysis of mammalian cells in some protocols.

Manual grinding is the most common method used to disrupt plant cells. Tissue is frozen in liquid nitrogen and then crushed using a mortar and pestle. Because of the tensile strength of the cellulose and other polysaccharides comprising the cell wall, this method is the fastest and most efficient way to access plant proteins and DNA.

Cells can be treated with various agents to aid the disruption process. Lysis can be promoted by suspending cells in a hypotonic buffer, which cause them to swell and burst more readily under physical shearing. Lysozyme (200 µg/ml) can be used to digest the polysaccharide component of yeast and bacterial cell walls. Alternatively, processing can be expedited by treating cells with glass beads in order to facilitate the crushing of cell walls. This treatment is commonly used with yeast cells. Viscosity of a sample typically increases during lysis due to the release of nucleic acid material. DNase can be added to samples (25-50 µg/ml) along with RNase (50 µg/ml) to reduce this problem. Nuclease treatment is not required for sonicated material since sonication shears chromosomes. Finally, proteolysis can be a problem whenever cells are manipulated; therefore, protease inhibitors should be added to all samples undergoing lysis.

Although physical methods have traditionally been used to disrupt cells, there are some inherent disadvantages to their use. Localized heating within a sample can occur with many of the techniques described, leading to protein denaturation and aggregation. To avoid this problem it is essential to pre-chill equipment and keep samples on ice at all times. Reproducibility with homogenization and grinding methods can be challenging due to inexact terminology used to define sample handling. Furthermore, cells disrupt at different times so the viscosity of the medium constantly changes, and released subcellular components are subjected to disruptive forces. In addition to sample handling problems, some physical disruption methods require fairly expensive equipment, such as the French press and sonicator.

2. Extraction of the Lysed Cells

In the preferred embodiment, the lysed cells are subjected to a cold extraction and phase separation.

The lysed cells are filtered through a filtration system at room temperature, passing the volume harvested through a 5 micron filter. The supernatant is removed and the remaining pellet is acidified with glacial acetic acid (e.g., 500 ml).

To fracture the pellet, the pellet is resuspended with shaking for 10 minutes and then frozen at −80° C. for approximately 24 hours. If the fracture is not complete, disruption can be performed at room temperature with pure nitrogen (grade 5) at a pressure between 1000 to 2000 PSI for 30 minutes. The precipitate and supernatant are separated by centrifugation (e.g., 4,400 RPM for 30 minutes). A sample of the supernatant is analyzed for phycotoxin (e.g., neosaxitoxin) content by HPLC.

Following separation, the extract is purified by preparative chromatographic column. For example, 50 mL of toxin extract is introduced to a column of Bio Gel P-2 fine (available from Bio Rad), which has a size exclusion limit of 1,800 Daltons. The column is eluted with acetic acid (e.g., 50 mL, flow rate of 13 mL/minute). Materials having a molecular weight greater than 1800 Daltons, such as cell components and pigments, are retained on the column, while the phycotoxins are eluted from the column. The resulting phycotoxin fragment typically contains a relatively small amount of contaminants (e.g., less than 30%). Typically, 5 fractions, each having a volume of approximately 50 ml), are obtained from a single sample. Each fraction is then analyzed by HPLC to confirm conformity to the specifications.

Following HPLC analysis, the volume of the combined phycotoxin fraction is reduced to approximately 50 mL. The sample is introduced to a cation exchange chromatographic column, such as a Bio Rex-70 (available from Bio-Rad). The column is treated with acetic acid (e.g., 500 ml with a flow of 13 mL/min) to obtain 15 fractions of 50 mL each, which are analyzed by HPLC.

3. Purification of the Cell Extract

The aqueous portion of the extract is then concentrated, typically using centrifugation, then passed through a diatomaceous earth column. The column is washed, for example, with 10 times its volume of 50 mM acetic acid. After the washing step, phycotoxin (e.g., neosaxitoxin) retained on the column is extracted with an alcoholic extraction mixture such as 2:1:1 vol/vol/vol ethanol:water:5 mM acetic acid.

The eluate from the column is passed through activated charcoal columns, which are washed with distilled water to remove the retained pigments and impurities. Any retained phycotoxins are eluted with an alcoholic elution mixture such as 3:2:1 vol/vol/vol ethanol:water:1 mM acetic acid at pH 5.

The eluate from the charcoal column is again passed through a diatomaceous earth column and washed with 50 mM acetic acid. Subsequently, the toxin is eluted from the column with a 1:1:1 vol/vol/vol chloroform:methanol:water mixture.

The organic solvents from the eluate from the second diatomaceous earth column are removed by evaporation. The partially purified neosaxitoxin is retained in the aqueous phase. The partially purified extract is subjected to a size exclusion preparative HPLC (preparative high-performance liquid chromatography).

III. Purified Phycotoxin

The processes described herein provide one or more purified phycotoxins. For those embodiments where the phycotoxin is a mixture of two or more phycotoxins, the relative amounts of the phycotoxins can be controlled in the production process, for example by the addition of one or more organic nutrients. Moreover, purification conditions can be varied to separate one or more phycotoxins from one or more other phycotoxins. In one embodiment, the process yields a mixture of neosaxitoxin/saxitoxin with a ratio of 8.47. In percentages, an average of 11.8% saxitoxin and 88.2% neosaxitoxin was obtained. These are then separated for formulation.

In the preferred embodiment, the formulations are for injection at a particular site for immediate relief from pain. In other formulations, these are formulated for topical or sustained release.

A. Sustained Release Compositions

In one embodiment, the compound(s) are formulated for sustained or extended release. Sustained or extended release dosage forms provides release of an effective amount of the compound(s) for an extended period of time, such as at least one week, two weeks, three weeks, four weeks, one month, two months, three months, four months, or six months. Sustained or extended release dosage forms can be administered parenterally, e.g., by injection, topically, or transdermally.

In one embodiment, the compound(s) are formulated as microparticles and/or nanoparticles that provide extended or sustained release of the compound. In some embodiments, the compounds can be incorporated into a matrix, wherein the matrix provides sustained or extended release. The matrix can contain one or more polymeric and/or non-polymeric materials. In other embodiments, microparticles and/or nanoparticles of drug can be coated with one or more materials that provide sustained or extended release.

Polymers which are slowly soluble in vivo and form a gel in an aqueous environment, such as hydroxypropyl methylcellulose or polyethylene oxide, may be suitable as materials for preparing sustained release drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the compound can be incorporated into microparticles prepared from materials which are insoluble in aqueous solution or slowly soluble in aqueous solution, but are capable of degrading by enzymatic degradation and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material which is normally solid at room temperature and has a melting point of from about 30 to 300° C.

In some cases, it may be desirable to alter the rate of water penetration into the microparticles/nanoparticles. To this end, rate-controlling (wicking) agents may be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropyl-cellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins which are water insoluble, such as zein, can also be used as materials for the formation of drug containing microparticles. Additionally, proteins, polysaccharides and combinations thereof which are water soluble can be formulated with drug into microparticles and subsequently cross-linked to form an insoluble network. For example, cyclodextrins can be complexed with individual drug molecules and subsequently cross-linked.

Encapsulation or incorporation of drug into carrier materials to produce drug containing microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. These processes are known in the art.

For some carrier materials it may be desirable to use a solvent evaporation technique to produce drug containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

Polysaccharides can also be cross-linked to form a water-insoluble network. For many polysaccharides, this can be accomplished by reaction with calcium salts or multivalent cations which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

B. Parenteral Formulations

The microparticles and/or nanoparticles can be formulated for parenteral administration, typically for administration by injection or direct application. Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, microemulsions, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

C. Injectable/Implantable Solid Implants

The compounds can be incorporated into injectable/implantable solid or semi-solid implants, such as polymeric implants. In one embodiment, the compounds are incorporated into a polymer that is a liquid or paste at room temperature, but upon contact with aqueous medium, such as physiological fluids, exhibits an increase in viscosity to form a semi-solid or solid material. Exemplary polymers include, but are not limited to, hydroxyalkanoic acid polyesters derived from the copolymerization of at least one unsaturated hydroxy fatty acid copolymerized with hydroxyalkanoic acids. The polymer can be melted, mixed with the active substance and cast or injection molded into a device. Such melt fabrication typically requires polymers having a melting point that is below the temperature at which the substance to be delivered and polymer degrade or become reactive. The device can also be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent. ATRIGEL® is another example of a formulation which forms a solid implant in situ upon contact with aqueous fluids.

Alternatively, the compound described herein can be incorporated into a polymer matrix and molded, compressed, or extruded into a device that is a solid at room temperature. For example, the compound can be incorporated into a biodegradable polymer, such as polyanhydrides, polyhydroalkanoic acids (PHAs), PLA, PGA, PLGA, polycaprolactone, polyesters, polyamides, polyorthoesters, polyphosphazenes, proteins and polysaccharides such as collagen, hyaluronic acid, albumin and gelatin, and combinations thereof and compressed into solid device, such as disks, or extruded into a device, such as rods. In other embodiments, the solid implant is in the form of a silastic implant.

The release of the compound from the implant can be varied by selection of the polymer, the molecular weight of the polymer, and/or modification of the polymer to increase degradation, such as the formation of pores and/or incorporation of hydrolyzable linkages. Methods for modifying the properties of biodegradable polymers to vary the release profile of the compound from the implant are well known in the art.

D. Topical Formulations

The compound can be administered topically. Suitable dosage forms for topical administration include creams, ointments, salves, sprays, gels, lotions, emulsions, and transdermal patches. The compositions may contain one or more excipients suitable for topical administration, such as chemical penetration enhancers, membrane permeability agents, membrane transport agents, emollients, surfactants, stabilizers, and combinations thereof.

"Emollients" are an externally applied agent that softens or soothes skin and are generally known in the art and listed in compendia, such as the "Handbook of Pharmaceutical Excipients", $4^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

Suitable classes of penetration enhancers are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

In some embodiments, the compounds can be applied topically in the form of a lotion, cream, gel, ointment, emulsion, or foam. These dosage forms typically contain hydrophilic and hydrophobic materials, for example, to form an emulsion.

"Hydrophilic" as used herein refers to substances that have strongly polar groups that readily interact with water. "Lipophilic" refers to compounds having an affinity for lipids. "Amphiphilic" refers to a molecule combining hydrophilic and lipophilic (hydrophobic) properties. "Hydrophobic" as used herein refers to substances that lack an affinity for water; tending to repel and not absorb water as well as not dissolve in or mix with water.

A "gel" is a colloid in which the dispersed phase has combined with the continuous phase to produce a semisolid material, such as jelly. An "oil" is a composition containing at least 95% wt of a lipophilic substance. Examples of lipophilic substances include but are not limited to naturally occurring and synthetic oils, fats, fatty acids, lecithins, triglycerides and combinations thereof.

A "continuous phase" refers to the liquid in which solids are suspended or droplets of another liquid are dispersed, and is sometimes called the external phase. This also refers to the fluid phase of a colloid within which solid or fluid particles are distributed. If the continuous phase is water (or another hydrophilic solvent), water-soluble or hydrophilic drugs will dissolve in the continuous phase (as opposed to being dispersed). In a multiphase formulation (e.g., an emulsion), the discreet phase is suspended or dispersed in the continuous phase.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) comprised of the drug dispersed or dissolved in a mixture of surfactant(s) and lipophilic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

The difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases which can produce flammable or explosive vapors during spraying. Furthermore, the compositions preferably contain no volatile alcohols, which can produce flammable or explosive vapors during use.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

For topical applications, repeated application can be done or a patch can be used to provide continuous administration of the compounds over an extended period of time.

Implants can be used to provide sustained delivery. In one embodiment, the implant is the Alza minipump; in another it is an insulin type pump; in still another embodiment, it is a silastic tube of the type used to deliver birth control hormones, such as IMPLANON®.

IV. Methods of Use

Phycotoxins, such as neosaxitoxin and saxitoxin, act as specific blockers of the voltage-dependent sodium channels present in excitable cells. Due to the inhibition of sodium channels, the transmission of a nervous impulse is blocked preventing the release of neurotransmitters at the neuromotor junction, which prevents muscular contraction. Due to these physiological effects, these compounds are potentially useful in pharmacology when used as muscular activity inhibitors in pathologies associated with muscular hyperactivity, such as muscular spasms and focal dystonias, when administered locally. These compounds can also inhibit sensory pathways and generate an anesthetic effect when administered locally.

EXAMPLES

Example 1

Phycotoxins Obtained and Purified from *Aphanizomenon gracile* Maintained in Continuous Cultures Under Controlled Conditions Methods and Materials In *Aphanizomenon gracile* cultures produced from a selected single clone, neosaxitoxin is the main phycotoxin produced, with smaller amounts of saxitoxin.

The production of neosaxitoxin from *Aphanizomenon gracile* cyanobacteria was carried out from an initial amount of 10 milligrams of wet *Aphanizomenon gracile* cells. The purification as conducted on a cell pellet.

For 10 mg of cell pellet, 10 mL of the same volume in weight of the mixture of organic solvents (1:1 chloroform: methanol+50 mM acetic acid in a 50% proportion with chloroform:methanol, resulting pH 5.0) were added to the cell pellet to destroy the cell wall and the cytoplasmic membrane. The lysed cells were subjected to a cold extraction and phase separation.

The extracted aqueous phase was concentrated 10 times by volume using a rotary evaporator at room temperature. The resulting concentrate was centrifuged at 20,000×g for 30 minutes.

2 mL of the supernatant from the centrifugation was passed through a diatomaceous earth column. The column was washed with 10 times its volume of 50 mM acetic acid. After the washing step, neosaxitoxin retained in the column was extracted with 5 mL of an alcoholic extraction mixture (2:1:1 vol/vol/vol ethanol:water:5 mM acetic acid).

The eluate from the column obtained was passed through activated charcoal columns, which were washed with distilled water to remove the retained pigments and impurities. Phycotoxins remain retained in the columns, and were eluted with 10 mL of an alcoholic elution mixture (3:2:1 vol/vol/vol ethanol:water:1 mM acetic acid) at pH 5.

The eluate from the charcoal column was again passed through a diatomaceous earth column and washed with 50 mM acetic acid. Subsequently, the toxin was eluted from the column with 5 mL of a 1:1:1 vol/vol/vol chloroform:methanol:water mixture.

The organic solvents from the eluate from the second diatomaceous earth column were removed by evaporation using a "speed vac" (Savant, N.Y., USA). The partially purified neosaxitoxin was retained in the aqueous phase. The partially purified extract was subjected to a size exclusion preparative HPLC (preparative high-performance liquid chromatography).

Results

After 2 days of culturing, each reactor produced an average of 652.4 micrograms of total toxin per each collected liter. The average neosaxitoxin/saxitoxin ratio was 8.47. In percentages, an average of 11.8% saxitoxin and 88.2% neosaxitoxin was obtained.

Figure 1:
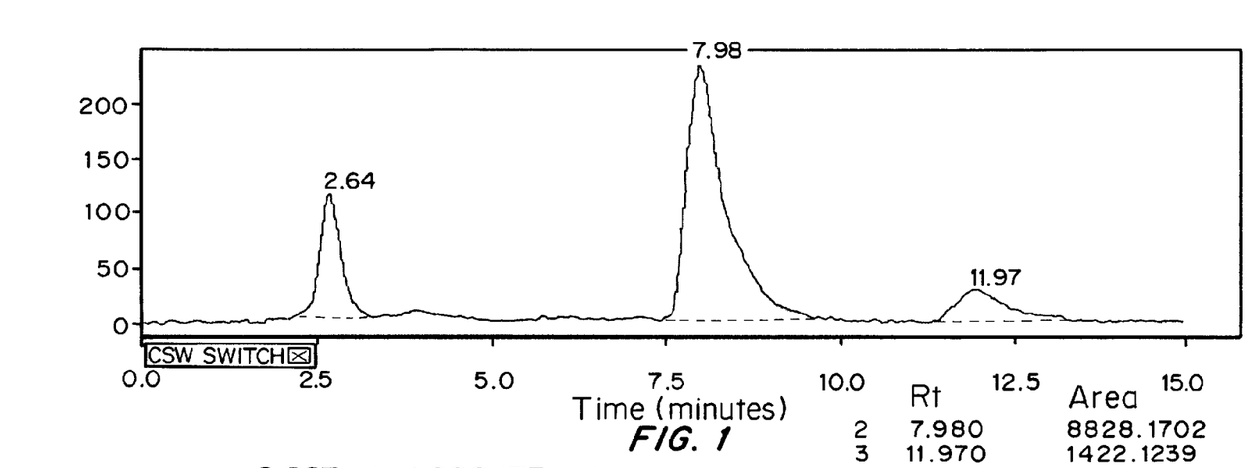
FIG. 1 is a chromatogram of an extract of the phycotoxins produced by the cyanobacterium *Aphanizomenon gracile* as analyzed high-performance liquid chromatography (HPLC) equipment. The detection method used was fluorescence online detection. Peak 1, RT=2.640 minutes, cyanobacterial pigments. Peak 2, RT=7.980 minutes, neosaxitoxin. Peak 3, RT=11.970 minutes, saxitoxin.
Figure 2:
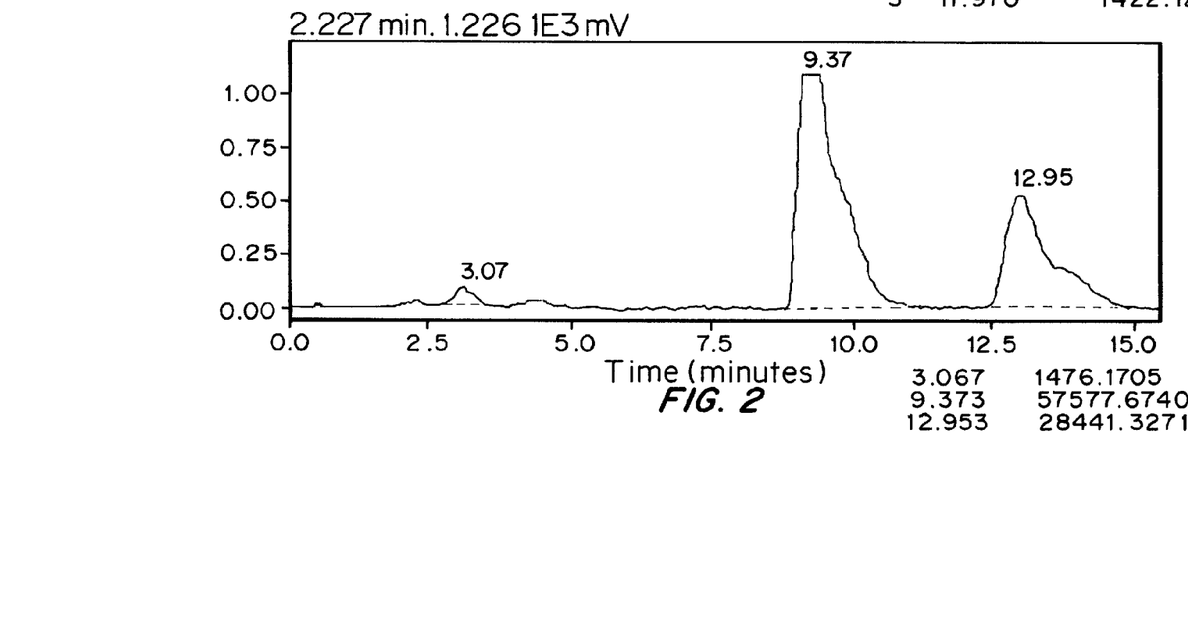
FIG. 2 is a chromatogram of 10 microliters of a purified extract from *Aphanizomenon gracile* purified by preparative size exclusion high-performance liquid chromatography (separation by molecular size). The detection method used was fluorescence online detection. Peak 1, RT=3.067 minutes, cyanobacterial pigments. Peak 2, RT=9.373 minutes, neosaxitoxin. Peak 3, RT=12.953 minutes, saxitoxin.
Figure 3:
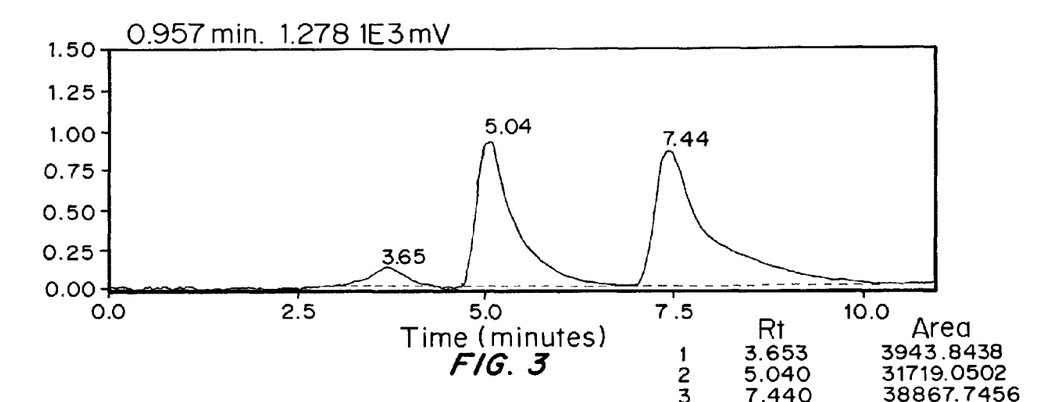
FIG. 3 shows a chromatogram of an analytical standard including neosaxitoxin and saxitoxin as its main components, with a small amount of a mixture of gonyaulatoxins (NL2 standard), determined and quantified by analytical high-performance liquid chromatography with online fluorescence detection. Peak 1, RT=3.653 minutes, mixture of gonyaulatoxins; peak 2, RT=5.040 minutes, neosaxitoxin; peak 3, RT=7.440 minutes, saxitoxin.
Figure 4:
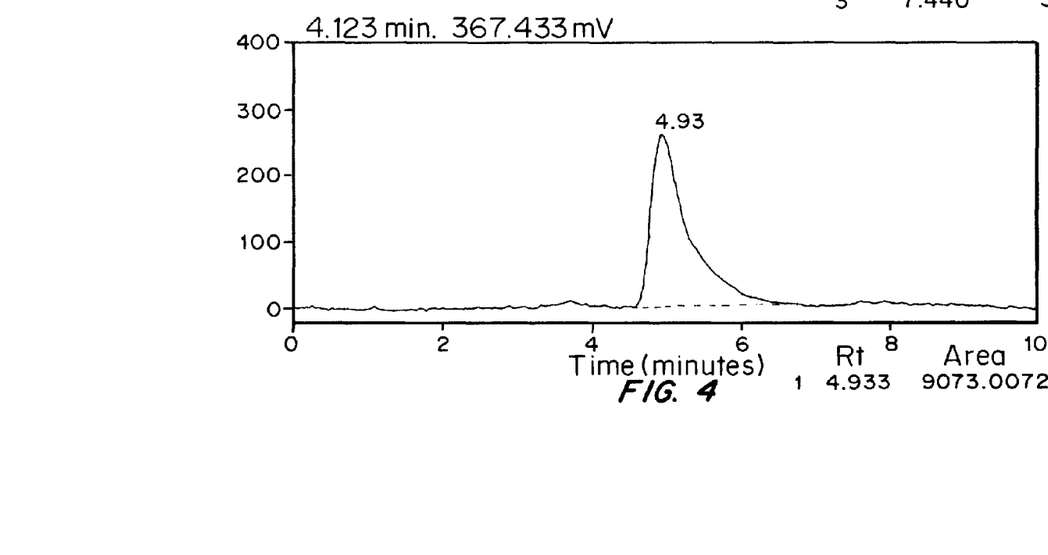
FIG. 4 is a chromatogram of a neosaxitoxin sample purified from extracts of *Aphanizomenon gracile* cyanobacteria (RT=4.933 minutes). This corresponds to the fraction eluted from a preparative high-performance liquid chromatography using ion exchange columns with online fluorescence detection.
Figure 5:
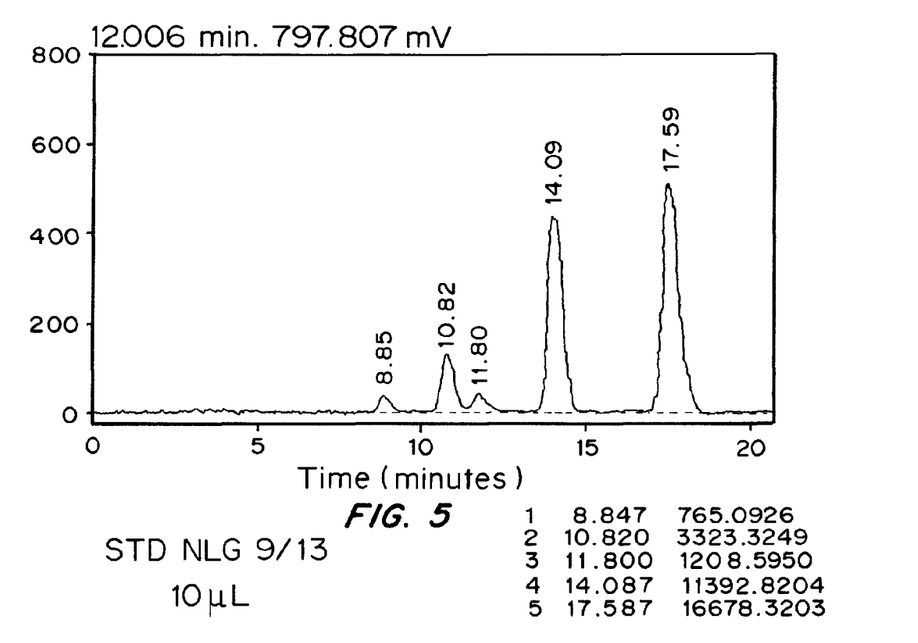
FIG. 5 shows a chromatogram of analytical standards of gonyaulatoxins. From left to right: Peak 1: GTX4 (gonyaulatoxin 4); Peak 2: GTX1 (gonyaulatoxin 1); Peak 3: GTX5 (gonyaulatoxin 5); Peak 4: GTX3 (gonyaulatoxin 3); Peak 5: GTX2 (gonyaulatoxin 2).

FIGS. 1, 2 and 4 show chromatograms of HPLC runs detected by online fluorescence detection that describe a phycotoxin profile produced by the species *Aphanizomenon gracile*. FIGS. 1 and 2 describe HPLC profiles of fractions presenting several degrees of purification from *Aphanizomenon gracile* extracts.

FIG. 1 shows a chromatogram of an unpurified *Aphanizomenon gracile* extract carried out to know and quantify the profile of phycotoxins present in this original extract. The chromatogram shows a simple profile with a major proportion of neosaxitoxin and a lower amount of saxitoxin (less than 13%).

FIG. 2 shows the purification of 10 microliters of an extract from *Aphanizomenon gracile* grown in continuous culture under controlled conditions, partially purified by preparative size exclusion high-performance liquid chromatography (separation by molecular size). In this partially purified extract, a typical peak at RT=9.373 minutes that saturates the chromatogram, which corresponds to neosaxitoxin, is already present, indicating the presence of a large amount of neosaxitoxin in this fraction.

FIG. 4 shows a neosaxitoxin sample purified from extracts of *Aphanizomenon gracile* cyanobacteria (RT=4.933 minutes) that is obtained in the fraction eluted from HPLC with ion exchange columns, corresponding the last purification step (final step of the method described above). A single peak is obtained, corresponding to a single component, which is pure neosaxitoxin in this case.

TABLE 2

Production of neosaxitoxin and saxitoxin as a function of the number of filaments and the wet weight of the *Aphanizomenon gracile* pellet

| neoSTX mM | STX mM | neoSTX µg/ml | STX µg/ml | neoSTX µg/fil. | STX pg/fil. | Cyano. fil./ml* |
|---|---|---|---|---|---|---|
| 8.98 | 3.50 | 2.83 | 1.05 | 2.42 | 0.90 | 1,170,000.00 |
| 13.66 | 4.91 | 4.30 | 1.47 | 3.44 | 1.18 | 1,250,000.00 |
| 3.42 | 1.03 | 1.08 | 0.31 | 1.71 | 0.49 | 630,000.00 |
| 17.82 | 4.78 | 5.61 | 1.43 | 9.42 | 2.41 | 596,000.00 |
| 17.81 | 4.02 | 5.61 | 1.21 | 13.17 | 2.83 | 426,000.00 |
| 7.66 | 1.47 | 2.41 | 0.44 | 4.94 | 0.91 | 488,000.00 |
| 10.87 | 2.19 | 3.42 | 0.66 | 10.25 | 1.97 | 334,000.00 |
| 10.52 | 2.07 | 3.31 | 0.62 | 4.38 | 0.82 | 756,000.00 |
| 10.77 | 1.96 | 3.39 | 0.59 | 7.47 | 1.30 | 454,000.00 |
| 17.24 | 2.99 | 5.43 | 0.90 | 13.12 | 2.16 | 414,000.00 |
| 5.31 | 0.41 | 1.67 | 0.12 | 5.19 | 0.38 | 322,000.00 |
| 12.26 | 2.17 | 3.86 | 0.65 | 9.47 | 1.59 | 408,000.00 |
| 9.84 | 1.94 | 3.10 | 0.58 | 17.42 | 3.27 | 178,000.00 |

STX: saxitoxin
neoSTX: neosaxitoxin
Cyano. fil.: cyanobacterial filaments
*Cyanobacterial filaments are associations of 20 to 100 cyanobacterial cells. These cyanobacteria form filaments in solution and those filaments are counted using the magnification of an inverted microscope.

The yields obtained represent a surprising unexpected production of pure phycotoxins (neosaxitoxin and saxitoxin) per milligram of wet cyanobacteria, when compared to the production of filaments and cyanobacterial pellets in usual culture conditions described so far in small culture flasks without continuous micro-aeration and with light:day and no light:night cycles. In the example described herein, cyanobacteria are always in the logarithmic growth phase, with permanent illumination 24 hours a day and with permanent collection of cyanobacteria, inducing permanent growth by adding new nutrients in a volume that is equivalent to the volume collected in each harvest.

Example 2

Phycotoxins Obtained and Purified from *Cylindrospermopsis raciborskii* Maintained in Continuous Cultures Under Controlled Conditions Methods and Materials The cyanobacterium *Cylindrospermopsis raciborskii* was cultured according to the continuous massive semi-automatic culture method under controlled conditions in permanent logarithmic growth, described in PCT/IB2010/05186, then purified as described in Example 1.

Results

Figure 6:
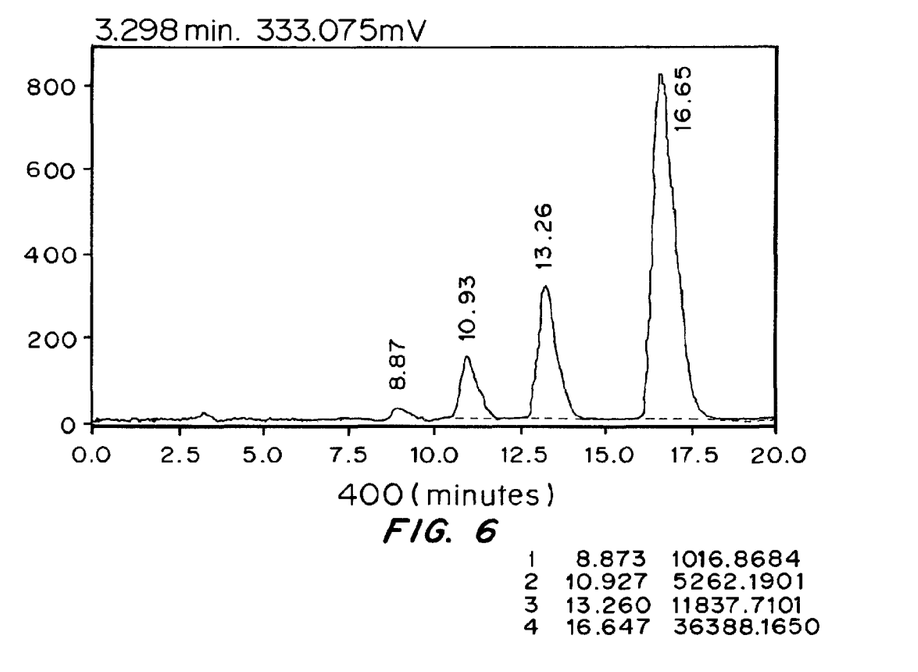
FIG. 6 shows a chromatogram of a sample of extract from the cyanobacterium *C. raciborskii*. Peak 1, RT=8.873 minutes, peak 2, RT=10.927 minutes, peak 3, RT=13.260 minutes; peak 4, RT=16.647 minutes.
Figure 7:
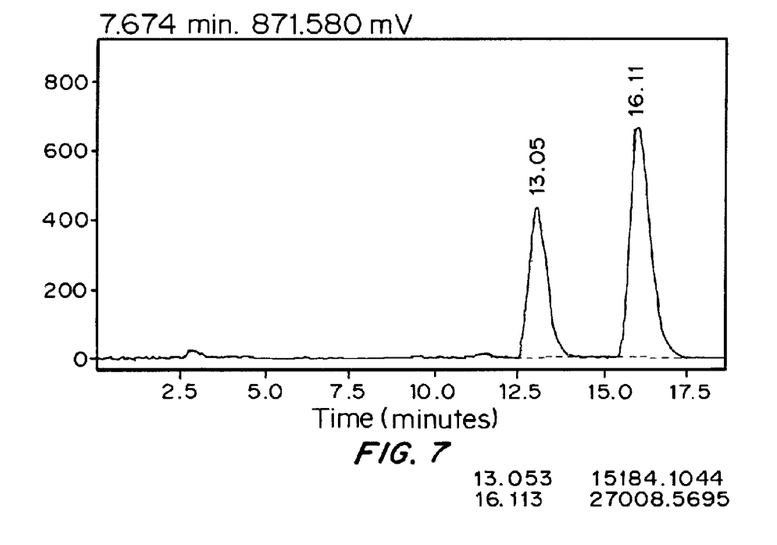
FIG. 7 is a chromatogram of a fraction from *C. raciborkii* partially purified by size exclusion high-performance liquid chromatography, with a dominant presence of the epimers GTX 3 and GTX 2, respectively.

The unpurified extract of the strain *Cylindrospermopsis raciborskii* has a chromatographic profile according to FIG. 6. *Cylindrospermopsis raciborskii* has a toxin profile where GTX 3 and GTX 2 are predominant, with the longest retention times in the column (the last two peaks at right, respectively). The *Cylindrospermopsis raciborskii* extract from the continuous culture is subjected to the purification process corresponding to the steps described for Example 1, and already at the size exclusion preparative HPLC step, the GTX3 and GTX2 epimers are almost exclusively obtained, as shown in FIG. 7.

Figure 8:
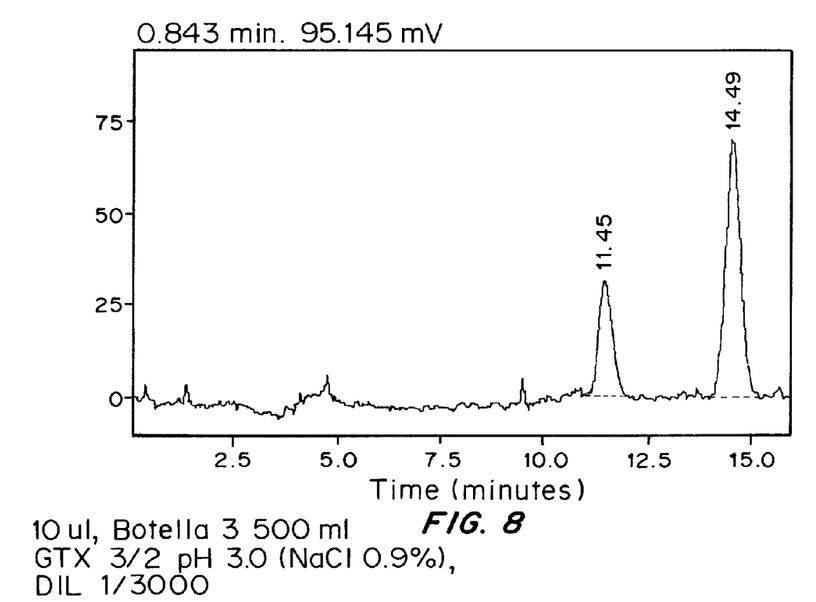
FIG. 8 shows a chromatogram of the final pure fraction of the epimers GTX 3 and GTX 2 obtained from a continuous culture of *C. raciborkii* cyanobacteria.
Figure 9:
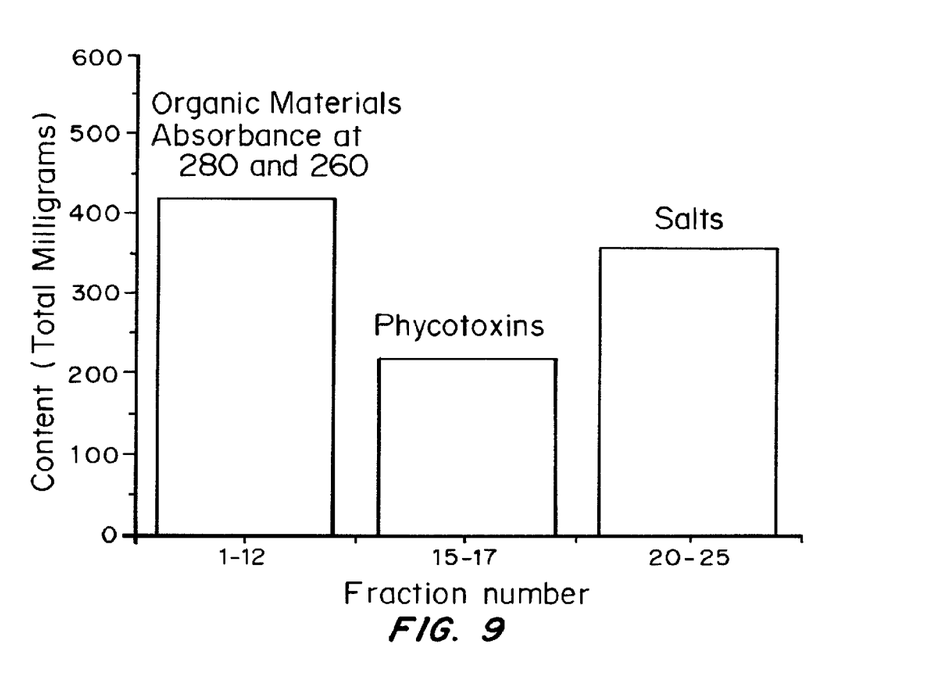
FIG. 9 shows an elution plot from a size exclusion preparative chromatography column showing the obtained fractions and identifying the range of fractions where the different compounds are present (organic compounds, phycotoxins and salts).
Figure 10:
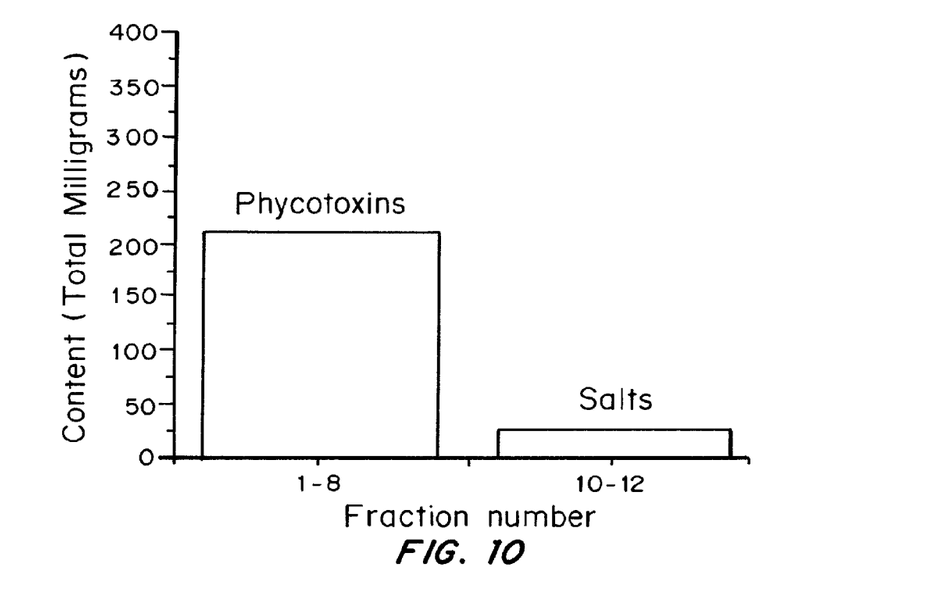
FIG. 10 shows an elution plot from an anion exchange preparative chromatography showing the obtained fractions and identifying the range of fractions where the different compounds are present (phycotoxins and salts).
Figure 11:
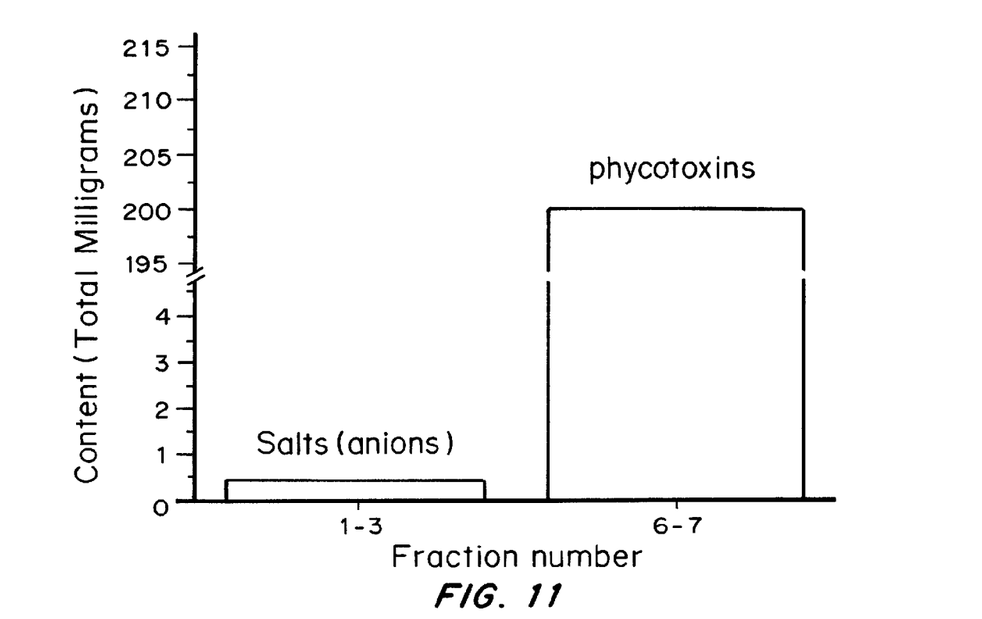
FIG. 11 shows an elution plot from a cation exchange preparative chromatography showing the obtained fractions and identifying the range of fractions where the different compounds are present (phycotoxins and salts).
Figure 12:
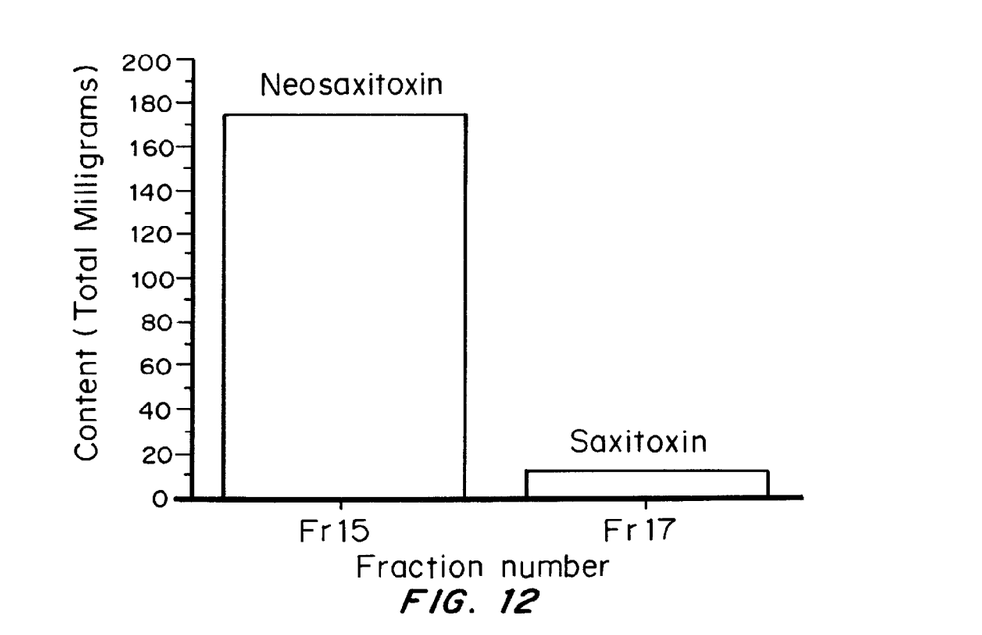
FIG. 12 shows an elution plot from a size exclusion preparative chromatography showing the obtained fractions and identifying the range of fractions where the different purified phycotoxins are present (saxitoxin and neosaxitoxin).

The final fraction of the phycotoxin purification method from *Cylindrospermopsis raciborskii* has only GTX3 and GTX2, as shown in FIG. 8 and fractions containing each gonyaulatoxin can be collected to obtain large amounts of pure GTX3 and GTX2.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A method for the isolation and purification of neosaxitoxin produced by cyanobacteria which produce neosaxitoxin and saxitoxin, the method comprising:
   (a) Lysing the cyanobacteria,
   (b) cold extracting the phycotoxins from the lysed cyanobacteria at pH 5 to obtain a concentrate,
   (c) passing the concentrate through a molecular weight separation column to obtain a phycotoxin eluate containing predominately neosaxitoxin, and
   (d) passing the eluate through a cation-exchange column, washing the column with acid and eluting the neosaxitoxin with an acidic alcoholic extraction solution to produce a highly pure neosaxitoxin eluant.

2. The method according to claim 1, in which the extraction in step (b) is repeated.

3. The method according to claim 1, further comprising passing the eluate of the molecular weight column or cation exchange column through a diatomaceous earth column washed with acetic acid and eluting the neosaxitoxin with an alcohol solution.

4. The method according to claim 1, further comprising passing the eluate of the molecular weight column or cation exchange column through activated charcoal and eluting the neosaxitoxin using an alcohol solution.

5. The method according to claim 3, in which the alcohol solution is a 1:1:1 vol/vol/vol chloroform:methanol:water.

6. The method according to claim 1, wherein the size exclusion chromatography has an 1,800 Dalton exclusion.

7. The method according to claim 1, wherein the cyanobacteria are selected from the group consisting of *Cylindrospermopsis* sp, *Microcystis* sp, *Anabaena* sp, *Gomphosphaeria* sp, *Oscillatoria* sp, *Aphanizomenon* sp and *Lyngbya wollei*.

8. The method of claim 1, wherein the concentrate obtained from step (b) contains less than 13% saxitoxin.

* * * * *